United States Patent
Müller-Späth et al.

(10) Patent No.: US 9,018,137 B2
(45) Date of Patent: Apr. 28, 2015

(54) METHOD FOR IDENTIFICATION AND PURIFICATION OF MULTI-SPECIFIC POLYPEPTIDES

(75) Inventors: Thomas Müller-Späth, Zürich (CH); Lars Aumann, Zürich (CH); Guido Ströhlein, Zürich (CH); Michael Bavand, Lenzburg (CH)

(73) Assignee: ChromaCon AG, Zurich (CH)

( * ) Notice: Subject to any disclaimer, the term of this patent is extended or adjusted under 35 U.S.C. 154(b) by 0 days.

(21) Appl. No.: 14/004,021

(22) PCT Filed: Mar. 15, 2012

(86) PCT No.: PCT/EP2012/054507
§ 371 (c)(1),
(2), (4) Date: Oct. 29, 2013

(87) PCT Pub. No.: WO2012/123520
PCT Pub. Date: Sep. 20, 2012

(65) Prior Publication Data
US 2014/0045725 A1   Feb. 13, 2014

(30) Foreign Application Priority Data
Mar. 17, 2011   (EP) ..................... 11158692

(51) Int. Cl.
*C40B 30/10*   (2006.01)
*C12N 15/10*   (2006.01)
*B01D 15/16*   (2006.01)
*B01D 15/18*   (2006.01)
*G01N 30/46*   (2006.01)

(52) U.S. Cl.
CPC .......... *C12N 15/1082* (2013.01); *B01D 15/166* (2013.01); *B01D 15/1807* (2013.01); *B01D 15/1864* (2013.01); *C07K 2317/31* (2013.01); *G01N 30/468* (2013.01)

(58) Field of Classification Search
None
See application file for complete search history.

(56) References Cited

FOREIGN PATENT DOCUMENTS

WO   2006/116886 A1   11/2006

OTHER PUBLICATIONS

Gunasekaran et al., Immunology: Enhancing Antibody Fc Heterodimer Formation Through Electrostatic Steering Effects: Applications to Bispecific Molecules and Monovalent IgG, J. Biological Chem., 2010, 19637-19646.*

(Continued)

*Primary Examiner* — Christian Boesen
(74) *Attorney, Agent, or Firm* — Sughrue Mion, PLLC

(57) ABSTRACT

The document pertains to a method for the purification of a ternary mixture of dimeric antibodies of the type AA, AB, BB, characterized in that for the separation of the three components and in particular for the isolation of the multi-specific fraction AB multicolumn counter current solvent gradient purification chromatography with a stationary phase load of more than 1 mg antibody mixture per milliliter stationary phase is used. It furthermore relates to a method for the identification of in particular bispecific antibody systems, which are particularly suitable for the application of such a purification method.

19 Claims, 5 Drawing Sheets

(56) References Cited

OTHER PUBLICATIONS

Thomas Miller-Spath, et al., "Chromatographic Separation of Three Monoclonal Antibody Variants Using Multicolumn Countercurrent Solvent Gradient Purification (MCSGP)", Biotechnology and Bioengineering, Aug. 15, 2008, pp. 1166-1177, vol. 100, No. 6.

T. Muller-Spath, et al., "Two Step Capture and Purification of IgG2 Using Multicolumn Countercurrent Solvent Gradient Purification (MCSGP)", Biotechnology and Bioengineering, Dec. 15, 2010, pp. 974-984, vol. 107, No. 6.

* cited by examiner

METHOD FOR IDENTIFICATION AND PURIFICATION OF MULTI-SPECIFIC POLYPEPTIDES

CROSS REFERENCE TO RELATED APPLICATIONS

This application is a National Stage of International Application No. PCT/EP2012/054507 filed Mar. 15, 2012, claiming priority based on European Patent Application No. 11 158 692.1 filed Mar. 17, 2011, the contents of all of which are incorporated herein by reference in their entirety.

TECHNICAL FIELD

The present invention relates to methods for identifying and purifying multi-specific polypeptides, in particular bispecific antibodies.

PRIOR ART

Antibodies are widely used for therapeutic purposes such as treatment of cancer and rheumatoid arthritis. Typically the antibody molecules comprise two sites for antigen recognition, both recognizing the same antigen.

Bispecific antibodies have been developed for therapeutic purposes that are capable of simultaneously recognizing two different antigens. The first bispecific antibody approved by regulatory authorities was Catumaxomab, a rat-mouse hybrid IgG. Its antigen recognition sites target a molecule on tumor cells (EpCAM) and a killer T cell, respectively, leading to effective tumor destruction. Due to their additional Fc receptor function, which is common to IgG antibodies, the bispecific antibody is considered to be tri-functional or tri-specific.

The chromatographic purification of such multispecific antibodies remains a major challenge since the different antibody types typically exhibit very similar adsorptive properties during chromatography. Furthermore, the complexity of antibody isoform combinations that may arise after expression of the different antibody chains makes purification of a single isoform species amongst other similar isoforms challenging.

SUMMARY OF THE INVENTION

It is therefore an object of the present invention to provide an improved purification method in particular for the purification of multifunctional multimeric antibody structures. It is a further object of the present invention to provide a method to identify and isolate particularly suitable multifunctional multimeric antibody structures. The term "antibody" includes in general any polypeptide allowing multispecificity binding functions and in particular fully human monoclonal antibodies, polyclonal antibodies, chimeric antibodies, humanized antibodies, single domain antibodies, minibodies and multispecific antibodies.

The present invention achieves this object by proposing a method of purification as claimed in claim 1 as well as by providing a method for the identification according to claim 7, i.e. by creating sufficiently diverse pools of heteromeric multi-specific antibodies or antibody-like scaffolds and then selecting, isolating and producing heteromultimeric polypetide species for pharmaceutical and therapeutical purposes.

Particularly, the present invention relates to a method for the purification of a ternary mixture of multimeric antibodies of the type AA, AB, BB (for the case of dimers), characterised in that for the separation of the three (or more) components and in particular for the isolation of the multi-specific fraction AB multicolumn counter current solvent gradient purification chromatography preferably with a stationary phase load of more than 1 mg antibody mixture per milliliter packed bed volume (stationary phase, firmly packed and including liquid) is used.

According to a first preferred embodiment, the antibodies are dimers formed from polypeptides A and B, the heterodimer being a bispecific antibody, each polypeptide A and B comprising a heavy polypeptide chain with at least one heavy chain variable region.

According to a further preferred embodiment, the antibody dimers may comprise a heavy polypeptide chain with at least one heavy chain variable region; and in addition a light polypeptide chain with a light chain variable region or a corresponding scaffold peptide.

According to a further preferred embodiment, the heavy polypeptide chain may also comprise at least one heavy chain constant region or a corresponding scaffold peptide. Such heavy chain constant regions can preferably be of the IgG, IgA, IgM, IgD or IgE class, wherein preferably the heavy chain constant regions are selected from the group of IgG1 and IgG4, or IgG1 and IgG2 subclasses.

According to another preferred embodiment of the method, a chromatographic stationary phase with a mean particle diameter of less than 70 micrometers is used, preferably of less than 50 micrometers, most preferably of in the range of 2-35 micrometers, wherein the width of the distribution ($2\sigma$) is preferably in the range of +/−50% of the mean value.

In single column chromatography, the process performance of the isolation of bispecific antibodies is often limited with respect to yield and productivity under a given purity constraint due to mass transfer and isotherm effects. In a chromatogram, this translates to peak overlap of the monoclonal and the bispecific antibody species which increases with increasing load. In order to improve yield and productivity and to better exploit the capacity of the stationary phase, a continuous process providing internal recycling of the overlapping fractions, such as the Multicolumn Countercurrent Solvent Gradient Purification (MCSGP) process, can be used beneficially. As mentioned above, the present invention also pertains to an identification or selection method for finding particularly suitable systems, for example to be purified in a process as outlined above. FIG. 3 in a schematic representation shows is the essential elements of the invented selection method, wherein two libraries A and B of monoclonal antibodies recognizing two different antigens are produced (top left boxes). For the specific situation of a ternary mixture as illustrated in FIG. 3 it is normally important that the monoclonal antibodies A and B have the same light chain and only distinguish in the heavy chain. If the antibodies comprise different light chains, the corresponding recombinations can e.g. yield 10 antibody types. The antibodies from each library are analyzed separately using a suitable method such as cation exchange chromatography (bottom left boxes). One of the ideas is that the antibodies from each library are essentially equal (pareto-optimal) with respect to the criteria affinity, specificity and stability, so that one is sure that those which are selected by analytical chromatography are also optimal. By comparing characteristic data obtained from the chromatograms, one monoclonal antibody candidate is chosen from each library and the DNA encoding for its heavy chains is transfected into host cells by means of a suitable vector together with the DNA encoding for the common light chain, and the host cells express the DNA and produce heavy and light chain polypeptides that associate randomly and form the heterodimeric desired bispecific antibody (A-B) and two homodimeric monoclonal antibody species (A-A, B-B), wherein the bispecific antibody may be isolated by single column or multicolumn continuous countercurrent chromatography, the latter being beneficial if the peaks of the homodimers and the heterodimer overlap.

The method described by the present invention enables the selection and preparative production of bispecific antibodies by preparative chromatography without requiring targeted mutagenesis to modify the amino acid sequence of the antibodies, allowing to preserve the natural sequence and reducing potential antigenicity of mutated sequences.

According to this element of the present invention, for the identification of a purifyable multi-specific polypeptide species (AiBj) which is a multimer consisting of at least two different specificity polypeptide chains (Ai, Bj), in particular a heterodimeric bispecific antibody, a method is used comprising the following steps:

(A) generation of a library of expression systems for each of the different specificity polypeptide chains (A, B) forming the multimer, preferably using array technologies, phage display, yeast display, ribosome display and variations thereof, and narrowing the library size through antigen binding and/or activity assays;

(B) individually expressing a sufficient amount of polypeptide chains (A1, A2, A3, . . . An; B1, B2, B3, . . . Bm) with each individual library member, and forming homomultimers therefrom, preferably homodimers (A1A1, A2A2, A3A3, . . . AnAn; B1B1, B2B2, B3B3, . . . BmBm) therefrom;

(C) using analytical methods, preferably chromatography, particularly preferably chromatography in single-column mode or isoelectric focusing (inclusive of HPLC and/or gradient methods), for the determination of an analytically discriminative parameter, preferably the chromatographic retention time, for each of the homomultimers;

(D) selecting at least one pair (AiAi, BjBj) of homomultimers of different specificity polypeptide chains which are analytically sufficiently discriminated;

(E) expressing the nuclear acids corresponding to the homomultimers identified in step (D) in host cells such that a mixture of homomultimers (AiAi; BjBj) and heteromultimers (AiBj) is produced by culture of the host cells;

(F) purifying the resulting ternary mixture by using chromatography, preferably using a chromatographic purification method as outlined above.

One of the important and preferred aspects here is that the antibodies from each library are essentially equal (pareto-optimal) with respect to selection criteria such as affinity, specificity, expressibility, avidity and stability (including aggregation properties, process stability, antibody stability etc.) and/or other criteria depending on the requirements of the specific case, so that one is sure that those which are selected by analytical chromatography are also optimal.

According to a first preferred embodiment of this method, the steps (A)-(D) are repeated until a pair can be identified, which is analytically sufficiently discriminated. For the discrimination in step (D) preferably a relative retention time in a chromatographic separation of smaller than 0.9 and larger than 1.1 is used. As a criterion for the selection in step (D) at least one of the following relative parameters can be used: resolution (Rs), relative retention time (RRT), retention time, retention time difference, retention volume purity.

According to yet another preferred embodiment, steps (A)-(F) are carried through repeatedly for the generation of a library of purifyable multi-specific polypeptide species, and out of these one or several are selected which show the best activity. Indeed sometimes it is not possible to discriminate between finally particularly active systems and less active systems using the discrimination in step (D). In this case the above mentioned steps are used for the generation of a library of systems and then these are scanned for active pairs which at the same time active and purifyable.

According to yet another preferred embodiment, the purifyable multi-specific polypeptide species (AiBj) is a bispecific antibody formed from polypeptides A and B, the heterodimer being a bispecific antibody, each polypeptide A and B comprising a heavy polypeptide chain with at least one heavy chain variable region.

According to yet another preferred embodiment, the antibodies are dimers formed from polypeptides A and B, the heterodimer being a bispecific antibody, each polypeptide A and B comprising: a heavy polypeptide chain with at least one heavy chain variable region; and a light polypeptide chain with a light chain variable region or a corresponding scaffold peptide.

Generally, the term "scaffold peptide" refers to any polymer of amino acids that exhibits properties desired to support the function of the antibody. This includes the addition of specificity, the enhancement of antibody function or the support of antibody structure and stability.

According to a further preferred embodiment, the heavy polypeptide chain comprises at least one heavy chain constant region or a corresponding scaffold peptide.

The heavy chain constant regions can be of the IgG, IgA, IgM, IgD or IgE class, wherein preferably the heavy chain constant regions are selected from the group of IgG1 and IgG4, or IgG1 and IgG2 subclasses. Each of the polypeptides (A,B) may comprise a heavy chain variable region and/or a corresponding scaffold peptide.

The multispecific antibody or scaffold may comprise a third polypeptide (C) comprising a light chain variable region and/or a scaffold, wherein a first polypeptide (A) and a second polypeptide (B) each form a multimer with said third polypeptide (C).

The first polypeptide (A) and the second polypeptide (B) may comprise a heavy chain constant region.

As mentioned above, the heavy chain constant regions of the polypeptides can be of different subclasses such as IgG1, IgG2 and IgG4.

Furthermore the present invention relates to a heterodimeric bispecific antibody (AiBj) determined using an identification method as outlined above and/or using a purification method as outlined above.

A preferred embodiment of the invention is the production of heterodimeric bispecific antibodies from two libraries of homodimeric monoclonal antibodies. The antibodies of each library are directed against different antigens as to allow for production of bispecific antibodies using the DNA of one antibody of each library. Each library should preferably contain more than 10 antibodies, preferably more than 30 antibodies and even more preferably more than 50 antibodies. All antibodies preferably contain the same L chain polypeptide and differ among each other in their H chains only.

All antibodies of each library are analyzed, preferably individually, with a suitable technique in order to obtain information allowing for a ranking of the antibodies for the production of bispecific antibodies. Preferably, the analysis of the monoclonal antibodies from each library is carried out by HPLC using a single column and linear gradient elution conditions. Preferably, in view of prospective semi-preparative or preparative scale manufacturing, the analysis is carried out using semi-preparative or preparative stationary phases. The mobile phase conditions for the analysis are chosen in such manner that the analysis for each of the selected antibodies is possible using the same mobile phase conditions. For this purpose the use of linear gradients from adsorbing to non-adsorbing conditions is preferred.

The detection of the eluting antibodies is done by spectroscopic methods including but not limited to UV absorption. The amount of antibody injected has to be above the detection limit of the instrument, preferably above 1 µg, more preferably above 10 µg.

Since the sequence and the structure of the antibodies are different, they exhibit different adsorptive properties with respect to the stationary phase and, consequently, different retention times. For each antibody the chromatogram is recorded and the retention time of the main peak maximum tRP, the retention time of the peak front start tRF, the retention time of the peak tail end tRT (for the definition of these parameters reference is made to the explanations given below, in particular to example 4 detailed below), the area of the main peak and the total area is recorded.

A preferred embodiment of the invented method includes a calculation of the purity of the antibody by dividing the area of the main peak which is given by the area in between the valleys between the main peak and the early and the late eluting neighboring peaks by the total area of all peaks together, as also indicated in FIG. 5. Preferably the purity is determined using an analytical stationary phase.

Subsequently, the retention time data of pairs of antibodies with one antibody from a library of antibodies against a first antigen (A-A) and the second antibody from a library of antibodies against a second antigen (B-B) is compared. Thereby each antibody of the first library is compared with each antibody of the second library, as to evaluate each possible combination. For the sake of clarity, in the following the antibodies of the first library are designated A1-A1, A2-A2, A3-A3, etc, while the antibodies of the second library are designated B1-B1, B2-B2, B3-B3, etc, according to their order in the analytics, or in general Ai-Ai and Bj-Bj, where i and j are integer numbers running from 1 to the number of antibodies in the respective library.

In the following, with regard to each pair of antibodies, the antibody with the smaller value of tRT is referred to as the "first" antibody while the antibody with the larger value of tRT is referred to as the "second" antibody. For the methods described in the following it is irrelevant which one of the antibodies Ai-Ai and Bj-Bj is eluting before the other. The retention times of the first antibody shall be referred to as tRF,1; tRP,1 and tRT,1 in the following, the values of the second antibody shall be referred to as tRF,2; tRP,2 and tRT,2.

In the following, it is shown how pairs of antibodies (Ai-Ai, Bj-Bj) are evaluated according to a resolution criterion.

"Resolution" is defined by the following formula for symmetrical, Gaussian peak shapes: Rs=2*(tRP,2−tRP,1)/(W1+W2), where W1 and W2 are the widths of the first and the second peak, respectively. For asymmetric peaks, this formula is no longer valid, and the retention times of the second and the first main peak have to be replaced by the mid-point of the baseline. Thus tRP,2 has to be replaced by (tRF2+tRT2)/2 and tRP,1 has to be replaced by (tRF1+tRT1)/2. Furthermore, the widths are given by W1=tRT1−tRF1 and W2=tRT2−tRF2.

With this, the resolution equation can be rewritten as Rs=(tRF2+tRT2−tRF1−tRT1)/(tRT1+tRT2−tRF1−tRF2). The resolution can now be calculated for each pair (Ai-Ai, Bj-Bj) and sorted in descending order. A value of Rs>1 indicates that the peaks are baseline-separated, a value of Rs=1 indicates a touching of the peaks at their baselines and a value of Rs<1 indicates a peak overlap.

The purity of each of the two antibodies of each pair, determined according to the method shown in Example 2 should be >70%, more preferably >80% and even more preferably >90%.

A simplified criterion, termed Δ(i,j) criterion, which is based on a single retention time difference can be used when all peaks Ai-Ai and Bj-Bj have similar widths, preferably differing by 25% at the most.

The calculations are carried out as follows: For each pair (Ai-Ai, Bj-Bj), the value of tRT,1 of the first antibody is subtracted from the value tRF,2 of the second antibody, the corresponding difference is called Δ(i,j). A value Δ(i,j)>0 indicates that the peaks are separated at the baseline. A value Δ(i,j)<0 indicates that the peaks of the two antibodies overlap. Subsequently the antibody pairs are ranked by their Δ(i,j) values in descending order starting with the largest positive values.

The purity of each of the two antibodies of each pair, determined according to the method shown in Example 2 should be >70%, more preferably >80% and even more preferably >90%. Antibodies from the pairs with the highest Rs or Δ(i,j) values, respectively, are preferred. In a preferred embodiment of the method, the purity criterion shall be prevailing over the Rs or Δ(i,j) criterion, respectively.

The difference between the Δ(i,j) and Rs criteria is that the Rs criterion directly takes into account the peak widths, that may strongly vary from antibody to antibody due to the presence of isoforms. Since, in most cases, the antibody purity and the peak width correlate, the Rs criterion is more powerful than the Δ(i,j) criterion and preferred since it contains information on the purity. Nevertheless, it is not recommended to abandon the independent evaluation of the purity and to apply the Rs criterion without the purity criterion.

The genes encoding for the H chains of the selected candidates are now transfected together with the genes encoding for the common L chain into host cells using a suitable vector. The cells are grown using suitable media and culture conditions. The host cells produce and secrete into the surrounding media a mixture of antibodies containing the original monoclonal antibodies from each library (A-A, B-B) and the bispecific antibodies combining the antigen specificities of both libraries (A-B). When the antibody concentration has reached the desired level the cell culture supernatant is harvested and clarified. Subsequently the bispecific antibody is purified by chromatography.

The bispecific antibody is purified from the mixture of the monoclonal antibodies and from other typical impurities such as host cell proteins, host cell DNA and media components by means of single column chromatography or continuous countercurrent chromatography, after a suitable pre-treatment or without such treatment.

In a preferred embodiment, the purification is carried out using the MCSGP process with cation-exchange stationary phases, preferably with the stationary phase that was used also in the cloning candidate selection process of the antibodies and using one or more additional chromatographic steps for polishing.

In another preferred embodiment, the antibody is purified by protein A affinity chromatography which removes a large part of the typical impurities. However, due to its specific mode of action of binding only certain IgG subclasses, in most cases the protein A step does not significantly contribute to the removal of the homodimeric monoclonal antibodies (A-A, B-B). After purification by protein A chromatography, the bispecific antibody A-B is isolated in a second chromatographic purification step, preferably using the stationary phase applied in the cloning candidate selection process. The second chromatographic step may be carried out either in single column batch mode or in continuous counter-current mode which is beneficial if an overlap between the antibodies A-A, A-B and B-B is observed in single column mode. The second chromatography step may be followed by a third purification step to produce bispecific antibody with the desired purity.

The purity of a bispecific antibody is defined as the mass percentage of the heteromeric antibody with respect to all antibodies of the mixture, heteromeric and homomeric.

Once the bispecific antibody has been purified it may be transferred into a suitable formulation for application as a pharmaceutical.

The term "stationary phase" refers to functionalized or non-functionalized particles of polymeric or inorganic composition, e.g. silica, that are typically sphere-shaped in the case of polymeric particles and amorphous in the case of inorganic particles and represent the backbone of the chromatographic material. In the case of functionalized particles, the adsorption of the product to be purified takes place through interaction with a ligand that is typically connected to the stationary phase backbone by linkers. The modes of interaction of the ligands include but are not limited to cation-exchange, anion-exchange, hydrophobic interaction, reversed phase, normal phase, multi-modality, affinity, hydrophobic charge interaction chromatography, and chromatofocusing.

These stationary phases are characterized by their average particle size and their relatively broad particle size distribution The term "analytical stationary phase" refers to stationary phases with average particle sizes below 10 μm. The term "semi-preparative stationary phase" refers to stationary phases with average particle diameters in the range of 10 μm to 30 μm, while the term "preparative stationary phase" refers to stationary phases with particle diameters of 30 μm or larger.

Typically analytical stationary phases are commercially available only in the form of pre-packed columns. Suitable analytical pre-packed columns include but are not limited to Propac wCX-10, 4×250 mm, Dionex, Sunnyvale, Calif., USA; Tosoh SP Stat, 5×100 mm, Tosoh, Tokyo, Japan; YMC BioPro SP-10, Kyoto, Japan; Mono S 5/50 GL, 5×50 mm, GE Healthcare, Uppsala, Sweden.

Semi-preparative and preparative stationary phases are also available as bulk materials. Suitable stationary phases include but are not limited to materials of the Fractogel series (Merck, Darmstadt, Germany) and the Source series (GE Healthcare, Uppsala, Sweden).

The bulk materials can be packed in standard columns according to the manufacturer's instructions. The standard columns include but are not limited to columns of the Tricorn series (GE Healthcare, Uppsala, Sweden).

The term "load" refers to the mass of polypeptide that is injected onto the stationary phase for the purpose of purification. Typically, the load is refers to the column volume packed with stationary phase which is also referred to as packed bed volume and is given in mg polypeptide per mL of packed bed volume. Generally, the loading phase is followed by a washing step and before the purified product is recovered in a subsequent elution step and the stationary phase is cleaned and re-equilibrated for the next loading phase.

The analytical methods for ranking the antibodies of each library include HPLC methods and the evaluation such as described above but also isoelectric focusing (IEF) methods. HPLC may be carried out using a suitable instrument, preferably with optimized dead volumes, such as the Agilent 1100 or 1200 series (Agilent, Santa Clara, Calif., USA).

In the case of gel IEF, the method may be carried out using a Phast system (GE Healthcare, Uppsala, Sweden) or a comparable device using the operating parameters and conditions recommended by the manufacturer. The method may also be carried out using a capillary IEF (cIEF) device such as the iCE280 device (Convergent Bioscience, Toronto, Canada). Following the isoelectric focusing, a suitable method for detecting the antibody is carried such as UV absorption measurement, Coomassie or silver staining according to standard protocols. In IEF, each monoclonal antibody appears as series of bands as it comprises multiple charged isoforms. Nevertheless, the $\Delta(i,j)$ and the Rs ranking method as reported above can be carried out in a similar fashion:

Instead of the retention times tR, the distance of the bands on the IEF gel with respect to the edges of the working section can be used. The method is independent of the orientation of the working section.

For each antibody the distance of the band of the first isoform LFB and the distance of the band of the last isoform LLB are recorded.

In the following, with regard to each pair of antibodies, the antibody with the smaller value of LLB is referred to as the "first" antibody while the antibody with the larger value of LLB is referred to as the "second" antibody. In analogy to the calculation of Rs and $\Delta(i,j)$ based on the retention time values, the corresponding values RsIEF or $\Delta IEF(i,j)$ can be calculated by replacing tRF,1 by LFB,1; tRT,1 by LLB,1; tRF,2 by LFB,2 and tRT,2 by LLB,2.

Subsequently the antibody pairs are ranked in descending order by their RsIEF or $\Delta IEF$ values, respectively, starting with the largest positive values.

In IEF, the purity of the antibody is measured by comparing the intensity of the band of the main isoform with the band intensity of the remaining isoforms.

The advantage of isoelectric focusing over HPLC methods is that multiple samples can be analyzed in parallel.

The disadvantage of gel IEF is that predictions of the chromatographic behavior during the final purification are possible only to a limited extent and in the case of gel IEF that the estimation of the peak width and the purity is less accurate.

The term "mobile phase" refers to suitable running buffers for the operation of the chromatographic process, taking into account the functionality of the stationary phases. The mobile phases include but are not limited to phosphate buffers, acetate buffers and TRIS buffers. The buffer initiating the product elution from the column preferably contains a low modifier concentration while the buffer at the end of the product elution preferably contains a high modifier concentration, thus representing a change in modifier concentration over time, also termed "modifier gradient". Typically the modifier gradient is generated by mixing a first buffer with low modifier concentration with a percentage of a second buffer with high modifier concentration that increases over time. The respective modifier includes but is not limited to inorganic salts such as sodium chloride in the case of ion exchange chromatography; acetonitrile, ethanol, iso-propanol in the case of reversed phase chromatography; water in the case of hydrophobic interaction chromatography; sodium citrate, sodium acetate and glycin in the case of affinity chromatography; sodium phosphate, potassium phosphate and sodium chloride in the case of multimodal chromatography.

The term "Multicolumn Countercurrent Solvent Gradient Purification", abbreviated "MCSGP" refers to the class of chromatographic purification processes described in WO/2006/116886 as well as in WO 2010/079060, the disclosure of which is expressly included into this specification as concerns these purification processes using, chromatographic columns.

Generally, the term "polypeptides" refers to peptides and proteins or fragments thereof with more than ten amino acids. The polypeptides may be obtained through expression by genetically modified or unmodified living cells or by chemical synthesis. Moreover, the polypeptides may be produced by subjecting the expressed or synthesized amino acid chains to further processing such as enzymatic treatment or chemical modification.

The genes encoding for the H chain or L chain of antibodies can be obtained from known sequences or from antibody libraries. Many antibody libraries with antibodies directed against a single antigen are either known or can be generated by those skilled in the art using selection/amplification techniques such as array technologies, phage display, ribosome display, or lymphocyte immunization. Methods to produce antibody libraries by phage display are described in Clackson et al., Nature 1991, 352: 624-628; Marks et al., J. Mol. Biol. 1991, 222: 581-597; Griffiths et al., EMBO J. 1994, 13: 3245-3260; Vaughan et al., Nature Biotechnology 1996, 14: 309-314. These methods include the use of single chain antibodies obtained from human antibody libraries. The libraries preferably contain antibodies comprising heavy chains with difference isoelectric points. Further difference in isoelectric points may be introduced by the use of different wild-type antibody subclasses for each library (e.g. IgG1, IgG2, IgG3, and IgG4 in the case of IgG) that naturally have different pIs.

In addition, known methods, such as methods that use eukaryotic cells as libraries (WO95/15393) can be used.

Methods based on lymphocyte immunization rely on the use of the antigen for performing the immunization of B-cells. The immunization may be carried out in vitro using human B-lymphocytes or in vivo using mammals by suitable methods that comprise injection of the antigen. The immunized monoclonal antibody-producing B-cells are isolated and fused to myeloma cells to obtain hybridoma cells (G. Kohler and C. Milstein, Methods Enzymol. 1981, 73: 3-46). DNA encoding for antibody variable regions can be then obtained from the mRNA of the monoclonal antibody expressing hybridoma cells using reverse transcriptase and PCR techniques. Genes encoding for complete antibody chains can be obtained by linking the DNA encoding for the variable regions with DNA encoding for antibody constant regions.

In addition, human antibodies with the desired specificity can be obtained by immunizing transgenic animals that carry a complete repertoire of human antibody genes (see e.g. WO93/12227, WO94/02602, WO96/34096, and WO96/33735). Furthermore, B-lymphocytes carrying human antibodies can be isolated from transgenic animals carrying human antibody gene repertoires (Mendez et al., Nat. Genet. 1997, 15: 146-156, US20100323401).

The term "antigen" refers to molecules that can be recognized by the variable region of antibodies. These molecules include but are not limited to proteins, peptides, fragments and aggregates of the latter two and lipopolysaccharides. The antigen may be linked to other molecules such as BSA or cells and administered with adjuvants for enhancement of the immunogenicity.

The terms "H chain" and "L chain" relate preferably to the immunoglobulin class IgG although they are not limited to the different immunoglobulin classes (IgA, IgD, IgE, IgG, and IgM) or subclasses such as IgG1, IgG2, IgG3, and IgG4.

The genes for H and L chains are integrated into suitable vectors, preferably expression vectors that are subsequently introduced into host cells by known methods such as electroporation, lipofection and calcium phosphate precipitation.

The genes encoding for the antibody H and L chains may be supplemented with DNA encoding for a signaling sequence that enhances the secretion of the antibody by the host cells. Furthermore, the antibody may be treated enzymatically within the cells by intrinsic enzymes or enzymes integrated by genetic recombination in order to change the amino acid sequence after the translation or to change the glycosylation of the antibodies. The host cells include mammalian cells (such as CHO, BHK, HeLa, HEK293), bacterial cells (such as *E. coli*), yeast (such as *Saccharomyces* and *Pichia*), fungal cells (such as *Aspergillus*), insect cells and plant cells. The cells are grown in suitable growth media (such as DMEM) and suitable culture conditions such as suitable temperatures and pH values. Typically suitable temperatures are in the range of 35 to 40° C. and suitable pH values in between pH 6.0 and pH 8.0. Containers for cell culture include but are not limited to T-flasks, roller bottles, wave bioreactors, disposable bioreactors, and glass and steel bioreactors. The typical cultivation time is in between 1 day and 15 days. During the cultivation, nutrient solution may be added, media may be exchanged and the bioreactor contents may be agitated or aerated or otherwise adjusted in order to maintain suitable living conditions for the cells.

The antibodies may be produced also in transgenic animals, preferably mammals such as transgenic sheep, goats, cattle, pigs, rabbits or mice or in plants such as transgenic tobacco. The produced polypeptides of interest are either present within the cells or secreted into the cell culture media. In the former case the cells have to be destroyed in order to harvest the polypeptides.

The cell destruction can be carried out by various methods applying mechanical, physical, and chemical stress or combinations thereof in order to disrupt the cells.

If the polypeptide of interest is present in the cells in form of inclusion bodies the inclusion bodies are harvested from the cell lysate, solubilized and refolded using refolding agents such as guanidinium hydrochloride or urea before further purification.

In general, prior to chromatographic purification the lysate or cell culture supernatant is clarified by centrifugation, filtration or ultrafiltration or combinations thereof to remove insoluble components and cells. Numerous methods for purifying the polypeptide of interest are available.

If expanded bed chromatography is applied, the clarification step may be omitted. Furthermore, precipitation steps for the desired polypeptide or for impurities may be included in the purification process including but not limited such as ammonium sulfate precipitation or other salting out methods, ethanol precipitation and precipitation using caprylic acid. In addition solvent extraction or crystallization may be applied.

The chromatographic purification of the desired polypeptides is carried out using either functionality described above and may include one or multiple steps. The chromatography may be carried out in single column mode, or in continuous mode such as continuous annular chromatography, SMCC (sequential multicolumn chromatography), or in continuous countercurrent mode such as SMB or MCSGP.

Typically the antibody purification process includes at least one virus filtration step and one diafiltration step prior to formulation of the polypeptide product.

The formulation includes transfer of the polypeptide into a stable form. This may be achieved by freeze-drying or by transfer into sterile solutions such as oligosaccharide or sodium chloride solutions that can be administered to patients as pharmaceuticals.

Excipients, stabilizers and adjuvants may be included in the formulation.

The formulated polypeptides are administered to the patients for preventing or treating diseases or for diagnostic purposes. The administration of the formulated peptides takes place preferably parenteraly with a suitable dosage.

The term "multispecific antibody" refers to an antibody that can specifically bind to at least two different types of antigens. The multispecific antibody preferably comprises two polypeptides with heavy chain variable regions recognizing different antigens and a third polypeptide comprising a light chain variable region. Preferably, an oligomer is formed by the first polypeptide and the third polypeptide and another oligomer by the second polypeptide and the third polypeptide. This includes bispecific antibodies such as bispecific IgGs.

The term "different antigens" is not limited to different antigen molecules but refers also to different epitopes on a single antigen molecule. Thus, according to this definition, antibodies recognizing different antigens include antibodies recognizing different epitopes on the same antigen molecule.

The method described in the invention can be applied beneficially for the production of bispecific antibodies of various types. Thus, the term "antibody" includes in general any peptide scaffold allowing multispecificity binding functions and in particular fully human monoclonal antibodies, polyclonal antibodies, chimeric antibodies, humanized antibodies, minibodies and multispecific antibodies. The antibodies or scaffolds of the present invention may be derived from humans or animals, plants or microorganisms. The term "Chimeric antibodies" refers to antibodies that comprise amino acid sequences derived from different species. An example is an antibody containing mouse variable regions and human constant regions of the heavy and light chains, respectively. The constant regions of the antibodies including the CH1, CH2, CH3 and CL domains preferably are of human origin.

The term "humanized antibodies" refers to antibodies that essentially have the same amino acid sequence as fully human antibodies except for the CDR regions that are derived from animals. The humanization is carried out by extracting the DNA encoding for the CDR regions from an animal source and integrating it into DNA encoding for a human antibody. In order to aid this integration DNA sequences may be synthesized that provide overlapping portions between animal and human antibody DNA. The antibody genes containing the ligated DNA can be expressed in host cells after introduction via a suitable vector carrying the genes.

Further modifications of the DNA of the antibodies may be carried out, in order to improve their properties, such as the antigen binding capability. Among these modifications are site-directed PCR and cassette mutagenesis (see for example, Kunkel (1985) Proc. Natl. Acad. Sci. USA 82: 488-492). The sequence homology between the mutated variable region and the original variable region should be as high as possible, preferably 80% or higher, even more preferably 90% and higher.

The antibody binding site contains six CDRs, three in the H chain variable region and three in the L chain variable region.

Antigen binding can occur also if the number of CDRs is reduced, however with a lower affinity. Thus, in the present invention, the term "antibodies" also covers oligomers with a reduced number of CDRs in the H chain variable region and/or in the L chain variable region.

The term "minibodies" relates to polypeptides carrying antigen recognizing parts. The minibodies preferably contain the H and the L chain variable regions. They include also antibody fragments. Examples for antibody fragments are Fab and Fab2. Antibody fragments can be obtained from complete antibodies by enzymatic digestion, for example with papain or pepsin (see Brennan et al., Science (1985) 229:81) or by genetic recombination methods using DNA encoding for the H and the L chain variable regions. Minibodies can be produced from antibodies or antibody fragments by enzymatic treatment or by introducing vectors encoding for the complete amino acid sequence of the minibody into suitable host cells such as E. coli or yeast.

Minibodies include also single chain Fv (scFv) polypeptides that are obtained by linking the variable parts of the H and the L chain that form together an antigen recognizing site (Hu et al., Cancer Research (1996) 56: 3055-3061, Pluckthun and Pack, Immunology (1997) 3: 83-105). A minibody may also contain two variable parts of the H chain and two variable parts of the L chain that are linked together (tandem scFv). Suitable linkers typically are peptides themselves and do not negatively impact the function of the antigen recognizing site.

The advantages of minibodies and antibody fragments relate mainly to their small size compared to Immunoglobulin antibodies, which affects pharmacokinetics and to their low production costs, as they can be also produced using bacterial cells (Harrison and Keshavarz-Moore, 2006, Annals of the New York Academy of SciencesVolume 782, Issue 1; Arne Skerra Current Opinion in Immunology Volume 5, Issue 2, 1993, Pages 256-262), or yeast cells (Ridder et al. (1995) Nature Biotechnology 13, 255-260).

The minibody formats include Fab, Fab', F(ab')2, Fv, and scFv (single-chain Fv) (Holliger P and Hudson P J (2005) Nature Biotechnology 23 (9) 1126-1136, Pluckthun and Pack (1997) Immunotechnology Volume (3) 2: 83-105), diabodies, sc(Fv)$_2$, triabodies (Hudson and Kortt (1999) Journal of Immunological Methods (1999) 231: 177-189), and tandem diabodies (Björn Cochlovius et al. 2000, Cancer Research (2000) 60:4336-4341).

The term "diabody" refers to an antibody that comprises two light chain variable regions and two heavy chain variable regions. The L chain variable regions are each linked to a H chain variable region by a peptide linker of a length that is too short to allow the formation of an antigen recognizing site. However, if the peptide linker length is in the range of five amino acids, two constructs of this type may associate to form a dimeric antibody with two antigen recognizing sites, which is called "diabody". When the H chain variable regions or the L chain variable regions are different, the two antigen recognizing sites are different, and a bispecific diabody has been generated. (P. Holliger et al., Proc. Natl. Acad. Sci. USA 90: 6444-6448 (1993); WO93/11161). Moreover, if the peptide linker length is in the range of one or two amino acids, three constructs of this type can associate to form a trimeric antibody with three antigen recognizing sites, which is called "triabody". If the peptide linker length is zero, i.e. no linker is present, four constructs of this type can associate to form a tetrameric antibody with four antigen recognizing sites, which is called "tetrabody". With increasing number of constructs, the size of the oligomer increases, improving the pharmacokinetics of the antibody (Le Gall, et al 1999. FEBS Letters 453 (1): 164-168.). Thus by using constructs with different H or L chain variable regions, tri- or tetraspecific antibodies may be generated.

In the present invention, the term "multispecific antibody" preferably relates to "bispecific antibodies" that have two different antigen recognizing sites. However, the antibodies may have additional functionality, such as effector functions of the Fc constant region in the case of bispecific IgGs, The term "bispecific antibodies" includes antibody constructs that comprise two different scFv or tandem scFv parts linked to an Fc constant region. These constructs resemble an IgG molecule but lack the CH1 and/or the CL domain.

Furthermore, the term "bispecific antibodies" includes bispecific single domain antibodies. Single domain antibodies lack the L chain and thus comprise only two H chain variable regions and a constant part. Some single domain antibodies, such as the ones obtained from camelid animals also lack the CH1 domain.

Single domain antibodies can be obtained by immunization of camelid animals such as camels, dromedaries, llamas, alpacas, guanacos or cartilaginous fish such as sharks with the desired antigen. By isolation of the mRNA encoding for the antibodies, reverse transcription and PCR, an antibody library can be generated. Using screening techniques like phage display or ribosome display, antibodies that bind to the antigens can be found. Alternatively single domain antibodies can be produced from libraries containing the complete ensemble of antibodies of non-immunized animals and applying in vitro affinity maturation. The antibody may then be humanized by to decrease the risk of immunological reaction upon administration to humans. Due to the large homology between camelid VHH and human VH parts, the extent of required humanization can be minimized. (Muyldermans (2001) Reviews in Molecular Biotechnology 74: 277-302).

Single domain antibodies may also be generated by recombinant methods from genes encoding for full antibodies of humans or animals, comprising also light chain parts.

However, the derivation of single domain antibodies from camelid animals or cartilaginous fish is preferred.

Bispecific single domain antibodies are single domain antibodies comprising two different H chain variable regions. They can be produced using host cells that carry the DNA encoding for the two different heavy chain variable regions as described above.

Single domain antibodies share beneficial properties that may prove useful in therapeutic applications, such as their extended CDR3 loop that allows for targeting hidden antigens. (Current Opinion in Pharmacology. 2008, 8:600-608)

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
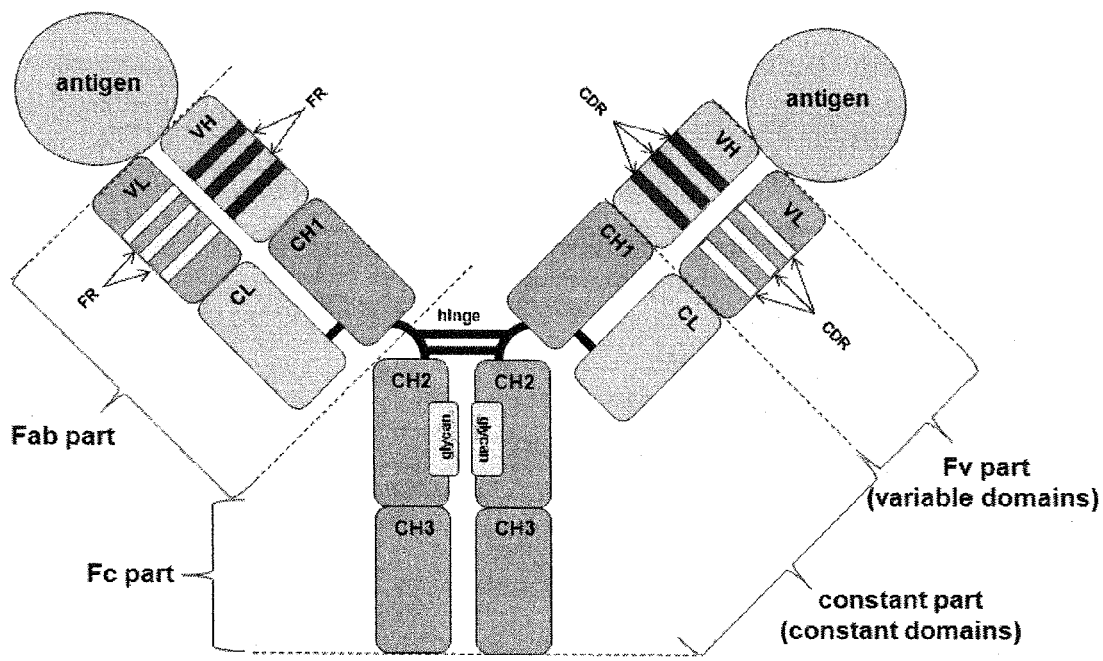
FIG. 1 shows a schematic illustration of a monoclonal antibody including two antigens.

Current antibody formats comprise heavy (H) and light (L) chains or at least their variable regions. IgG type antibodies are dimers consisting of two H and two L chains. The antigen recognition site is formed at the N terminus by each H and L chain pair (FIG. 1). In the case of monoclonal IgG antibodies, identical H and identical L chains are present, thus giving rise to the two identical antigen binding sites. In the case of bispecific IgG antibodies, the H chains or the L chains or both are not identical, forming two different antigen recognition sites.

A number of techniques are used in order to identify DNA encoding for H and L chains that lead to the formation of antigen recognition sites with the desired specificity. Among these screening techniques are phage display techniques, ribosome display techniques or techniques for isolating the DNA from antibody-producing B-lymphocytes. As state of the art, antibodies are produced in genetically modified host cells.

Since the contribution of the H chain to antigen recognition is the predominant one, the screening is frequently limited to the H chain. Criteria for selecting H chain candidates include the activity and the affinity and/or avidity for the antigen, the antigen specificity, low off-rates, good solubility, little aggregation, and good expressibility in the host cell system. Typically, each screening delivers several H chain candidates that are satisfactory with regard to these criteria. However, these candidates differ with respect to their amino acid composition which leads to differences in their physico-chemical properties such as the isoelectric point.

For each different antigen recognition site of the desired antibody, one H chain library is generated. Thus, for bispecific antibodies, two libraries of H chains are generated.

For production of IgG bispecific antibodies, one H chain is selected from each library and the corresponding DNA is integrated into suitable vectors and transfected into the host cells together with DNA corresponding to L chains. The cells produce the H and the L chains which randomly associate within the cells, giving rise to full IgG antibodies consisting of two H and two L chains which finally are secreted. Thus, due to the random association, apart from the desired bispecific antibody a number of unwanted antibody types is produced. The presence substantial quantities of unwanted antibody types with close similarity increases the complexity of the production process and decreases the yield of the actual desired antibody type, leading to increased production costs and cost of goods.

In order to minimize the number of unwanted antibody types in bispecific antibody production, a number of approaches can be used.

Firstly a common L chain, that maintains the antigen specificity of both antigen recognizing sites, is used for pairing with the H chains. This reduces the number of antibody types from ten to three and the proportion of the bispecific H chain heterodimer increases up to 50%.

Secondly the knobs-into-holes technique is applied to promote heterologous association of the H chains. Essentially, this technique comprises genetic modification of the H chain genes in such manner that at the association site in the CH3 region the H chain with the first specificity ("chain A") contains at least one amino acid with a bulky side chain (knob) while the H chain with the second specificity ("chain B") contains at least one amino acid with a small side chain (hole). For bispecific IgG production by combining the former two techniques, the proportion of the desired A-B heterodimer can be increased up to 95% while the remaining 5% consist of A-A and B-B homodimers. However, for use as biopharmaceuticals the purity of the A-B heterodimer has to be increased even further, which is achieved by removal of the homodimers from the antibody mixture in one or more chromatographic steps. However, the chromatographic purification still remains a major challenge since the different antibody types typically exhibit very similar adsorptive properties during chromatography.

Figure 2:
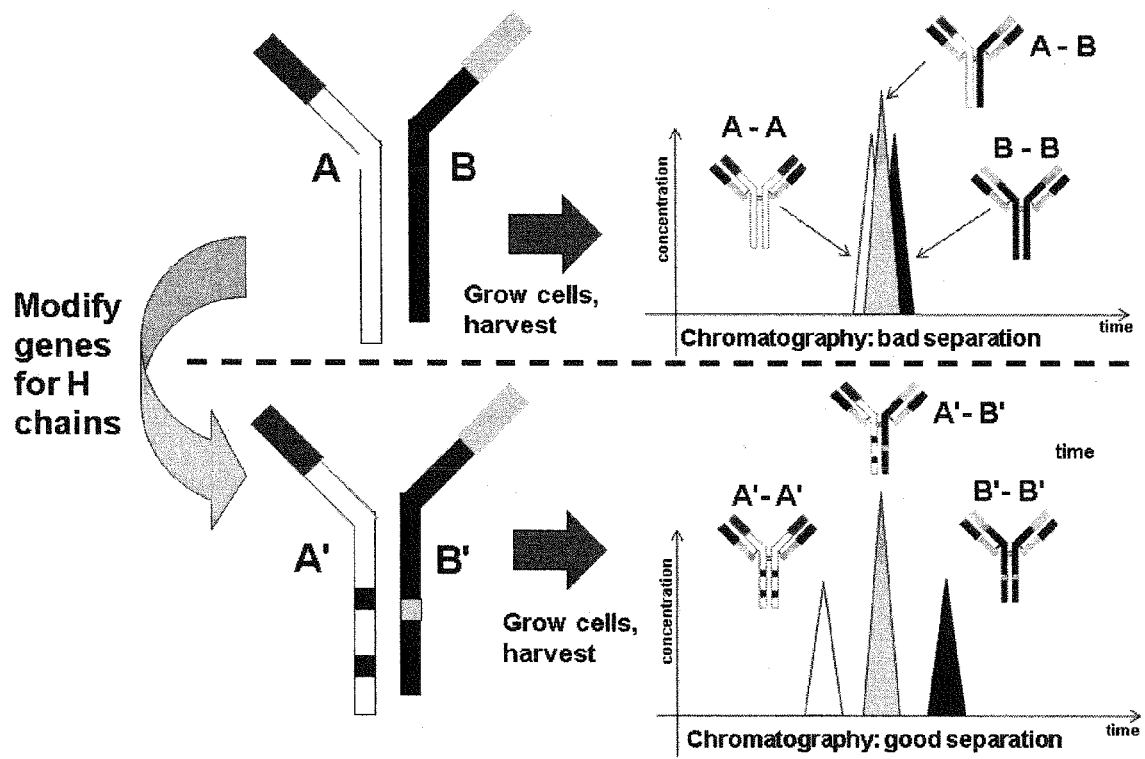
FIG. 2 shows a schematic illustration of the effect of amino acid modification of the H chains on the chromatographic purification of a bispecific antibody, wherein the upper part of the figure shows the chromatogram for a separation of heterodimeric bispecific antibodies (A-B) and homodimeric monoclonal antibodies (A-A, B-B) expressed from non-modified H chains (A, B), and the lower part of the figure shows the chromatogram for a separation of heterodimeric bispecific antibodies (A'-B') and homodimeric antibodies monoclonal (A'-A', B'-B') expressed from modified H chains (A',B') as described in US 20090263392.

To overcome this challenge, a further method as disclosed in US 20090263392 to improve the chromatographic purification of bispecific antibodies comprises firstly the modification of the amino acids that constitute the two H chains of the antibody through genetic recombination techniques in order to increase their difference in their isoelectric points, secondly the expression of the antibodies in host cells and thirdly the purification of the bispecific antibodies by chromatography. An increased difference of the isoelectric points of the two H chains leads to increased charge differences of the A-A homodimer, the A-B heterodimer and the B-B homodimer, which can be exploited for instance by ion exchange chromatography. The effect of the amino acid modification on the chromatographic purification performance is illustrated in the schematic in FIG. 2.

Use of different chromatographic functionalities is possible including affinity chromatography, hydrophobic interaction chromatography, thiophilic affinity chromatography, antigen affinity chromatography and ion-exchange chromatography.

The purification of the A-B heterodimer by protein A affinity chromatography is e.g. possible for the case of a heterodimer comprising a mouse IgG2a chain on the one hand and a rat IgG2b chain on the other. Since protein A has a high affinity for mouse IgG2a and a low affinity for rat IgG2b, the heterodimer has an intermediate affinity and can be eluted from the protein A stationary phase at intermediate elution strength.

The disadvantages of this method are its limitation to different IgG subclasses and to IgG subclasses from different non-human sources (mouse, rat), which increases the risk for antigenicity.

The purification of the A-B heterodimer by hydrophobic interaction chromatography has been demonstrated for the case of a heterodimer comprising a mouse IgG2a chain on the one hand and mouse IgG1 chain on the other. However, experimental results show that the separation between the desired heterodimer and the homodimers is not sufficient. A purification of an A-B heterodimer comprising two monomers of the same subclass, e.g. two IgG1 monomers, by hydrophobic interaction chromatography has so far not been described.

The purification of the A-B heterodimer by thiophilic affinity chromatography has been demonstrated for the case of a heterodimer comprising a mouse IgG1 chain on the one hand and rat IgG2a chain on the other. Since the technique requires the presence of free cysteines in the antibodies is not a general method and cannot be used for the heterodimers with H chains of the same subclass. Furthermore, proteins with free cysteines are prone to aggregation during the biopharmaceutical production process.

The purification of the A-B heterodimer by antigen affinity chromatography has been demonstrated nd is based on the use of immobilized antigens as ligands and requires two chromatographic steps. In the first step, the A-B heterodimer and one of the homodimers, for instance A-A, binds to the ligands, while the B-B homodimer is not bound to the ligand and removed by washing. In the second step, only the heterodimer is bound and the remaining homodimer is removed through washing. Since this method uses two chromatographic steps and requires customized stationary phases it is very costly at a manufacturing scale. Moreover it cannot be used for antibodies with high activity but low affinity.

The satisfactory isolation of A-B heterodimers with H chains belonging to the same subclass in combination with the targeted modification of the amino acid composition has been demonstrated wherein the isolation of the amino-acid-modified A-B heterodimer by ion exchange chromatography is used, using an analytical stationary phase and a preparative stationary phase. More precisely, in analytical cation exchange chromatography, the retention time for both the unmodified humanized A69 antibody homodimer and the humanized B26 antibody homodimer is the same, and thus separation of these homodimers and the desired bispecific antibody is impossible. On the other hand the chromatograms of antibodies with modified amino acids in the variable region of the H chains display peak shifts of the homodimers. This difference increases with the number of charge modifications made. Thus, the charge modification of the amino acid sequence of the H chains of the A69 and the B26 antibody, both belonging to the same IgG subclass, enables the separation of the homodimers and the isolation of the bispecific heterodimer. The modification may be carried out in the framework region (FR) or the complementary determining region (CDR) of the antigen recognizing part of the H chain requiring.

Chromatography as described in all cases above relates to single column batch mode and so far in this field no use of continuous counter-current chromatography has been reported. The two continuous counter-current chromatography processes reported include Simulated Moving Bed (SMB) chromatography and Multicolumn Countercurrent Solvent Gradient Purification (MCSGP), (see e.g. 05405327.7, EP 05405421.8). The isolation of bispecific antibodies requires the purification of a product component from a mixture containing impurity components with very similar adsorptive properties. As the bispecific heteromeric antibody in terms of adsorptive properties represents an average between the homodimeric antibodies, it will elute between the homodimers which makes the isolation more challenging since it requires a three fraction (ternary) separation.

Although pseudo-ternary separations have been reported for SMB with one of the impurities having very different adsorptive properties as the product, SMB cannot be used to isolate a product overlapping with early and late eluting impurities. In contrast, this capability has been demonstrated by MCSGP. Due to the counter-current movement between the mobile and stationary phases and the internal recycling of impure side fractions, with MCSGP the product can be isolated from the accompanying early and late side components achieving high purity and high yield simultaneously, even if the corresponding single column chromatogram shows a strong overlapping of the product and the impurity peaks. Application examples for MCSGP include the separation of monoclonal antibody variants or the purification of peptides produced by chemical synthesis.

In summary, chromatographic approaches to isolate a bispecific heterodimeric antibody from a mixture containing also the homodimeric forms have been successful only in limited cases, for instance if different H chain subclasses were used in order to introduce diversity of the monomeric and the heteromeric antibodies with respect to adsorptive properties in chromatography. A method for production and chromatographic isolation of a heterodimeric bispecific antibody comprising a single H chain subclass, suitable for production scale manufacturing and satisfying pharmaceutical product standards has not been reported, apart from the method described in US 2009/0263392. The isolation of bispecific antibodies from a mixture of antibodies, all carrying the same H chain subclass has proven challenging, since the antibodies can be separated only by their differences in their variable regions. Since the sequence homology of the variable regions is large, US 20090263392 suggests the modification of the amino acid sequence of antibodies with the desired specificity in order to alter the charge differences between the variable regions of the H chains involved on the antibody formation. This decreases the homology and may potentially decrease the activity of the antibody while the risk of immunogenicity increases making subsequent activity testing imperative. Thus, beneficial properties of the antibody are sacrificed in favor of a better separability in the chromatographic purification process.

Figure 3:
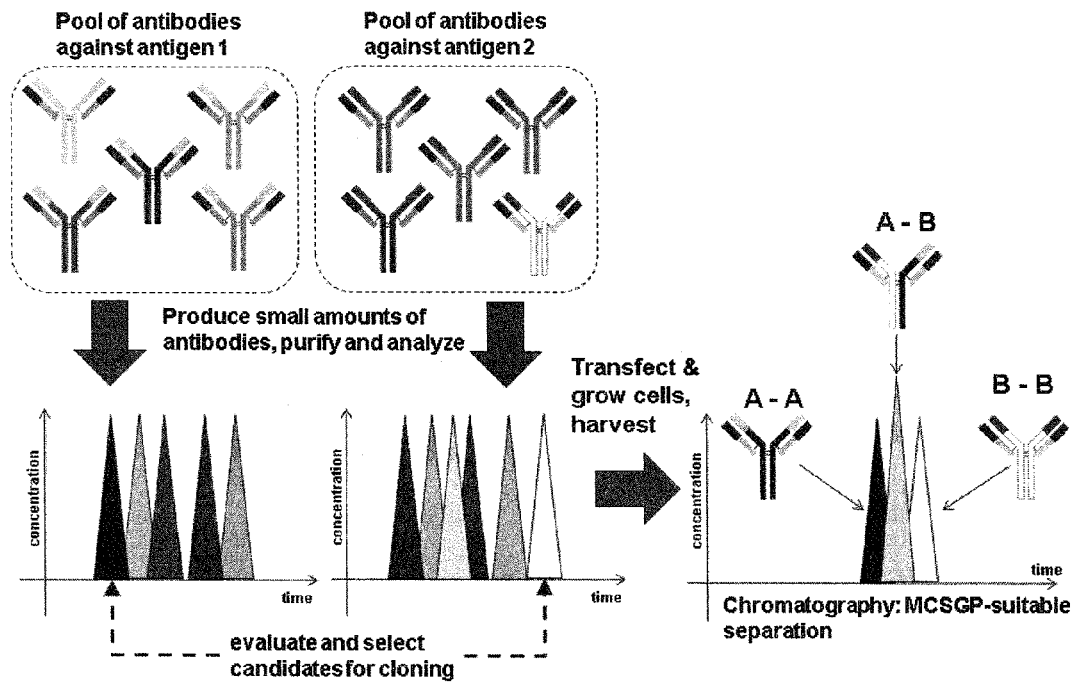
FIG. 3 shows a schematic illustration of the invented method, wherein two libraries of monoclonal antibodies recognizing two different antigens are produced, the antibodies from each library are analyzed separately using a suitable method such as cation exchange chromatography, by comparing characteristic data obtained from the chromatograms, one monoclonal antibody candidate is chosen from each library and the DNA encoding for its heavy chains is transfected into host cells by means of a suitable vector together with the DNA encoding for the common light chain, and the host cells express the DNA and produce heavy and light chain polypeptides that associate randomly and form the heterodimeric desired bispecific antibody (A-B) and two homodimeric monoclonal antibody species (A-A, B-B), wherein the bispecific antibody may be isolated by single column or multicolumn continuous countercurrent chromatography, the latter being beneficial if the peaks of the homodimers and the heterodimer overlap.

As mentioned above, the present invention takes a completely different approach to identify or select particularly suitable systems, for example to be purified in a process as outlined above, and this is summarized in FIG. 3 in a schematic representation: two libraries A and B of monoclonal antibodies recognizing two different antigens are produced (top left boxes). The antibodies from each library are then analyzed separately using a suitable method such as cation exchange chromatography (bottom left boxes). One of the key ideas here is that the antibodies from each library are essentially equal (pareto-optimal) with respect to selection criteria such as affinity, specificity, expressibility, avidity and stability (including aggregation properties, process stability, antibody stability etc.) and/or other criteria depending on the requirements of the specific case, so that one is sure that those which are selected by analytical chromatography are also optimal. By comparing characteristic data obtained from the chromatograms, one monoclonal antibody candidate is chosen from each library and the DNA encoding for its heavy chains is transfected into host cells by means of a suitable vector together with the DNA encoding for the common light chain, and the host cells express the DNA and produce heavy and light chain polypeptides that associate randomly and form the heterodimeric desired bispecific antibody (A-B) and two homodimeric monoclonal antibody species (A-A, B-B), wherein the bispecific antibody may be isolated by single column or multicolumn continuous countercurrent chromatography, the latter being beneficial if the peaks of the homodimers and the heterodimer overlap. This method enables the selection and preparative production of bispecific antibodies by preparative chromatography without requiring targeted mutagenesis to modify the amino acid sequence of the antibodies, allowing to preserve to a large extent the natural sequence and reducing potential antigenicity of mutated sequences. This shall be illustrated in more detail in the examples given below.

EXAMPLES

Example 1

Establishing Libraries of Monoclonal Antibodies by Phage Display

In the following the isolation of high affinity antibodies from a phage display library of the heavy chain variable and the light chain variable segments (VH and VL, respectively) is described.

In a first step, B-cells are obtained from human donors or from immunized animals such as mice or camelids as described in by Marks et al (1991) in J. Mol. Bio. 222, 581-597. Also synthetic libraries from cloned human variable chain segments may be used (Winter G. et al Annu. Rev. Immunol. 1994. 12:433-55).

Subsequently, VH and VL mRNA is obtained from the cells and transcribed separately into cDNA using PCR with suitable primers as described by Marks et al (1991 loc. cit.). Tagged primers to incorporate restriction sites in order to facilitate future ligations may be used advantageously as described by Vaughan et al. (1996), Nat. Biotech. 14, 309-314.

In order to obtain single chain Fv (scFv) fragments consisting of one VH and one VL chain, linker DNA such as DNA encoding for (Gly4Ser)$_3$ (Huston et al. (1988) Proc. Natl. Acad. Sci. 85, 5879-5883) is amplified by PCR either separately Marks et al (1991 loc. cit.), or together with the DNA encoding for one of the variable segments (Vaughan et al. (1996 loc. cit.)) to facilitate the construction of the library.

The VH, VL and linker DNA fragments are then assembled using PCR to form scFv genes. Afterwards, the scFV DNA is ligated with phage vector DNA such as pCantab 6 (Mc Cafferty et al. (1994) Appl Biochem Biotechnol. 47 (2-3): 157-171) or pHEN1 (Hoogenboom et al. (1991) Nucleic Acids Research, Vol. 19, No. 15 4133-4137) using restriction enzymes Using this technique, libraries of more than $10^{10}$ individual recombinants have been reported (Vaughan et al. (1996, loc cit)). By using combinatorial infection, even larger libraries of $10^{12}$ individual recombinants have been reported (Winter G. et al 1994 loc cit) The DNA constructs are introduced into of E. coli bacterial cells by electroporation or other suitable means and the cells are grown using a suitable media. Depending on the locus of the fusion of the scFv DNA and the phage DNA, phage rescue is required (Winter G. et al 1994 loc cit). Phage rescue may be performed using a helper phage such as M13 KO7 (Marks et al (1991 loc cit)).

The obtained library phages are then applied to a surface containing immobilized antigen (Vaughan et al. (1996 loc cit)). By repeated washing, only the phage expressing the antibodies with the largest affinity for the antigen remain bound and are recovered in a separate elution step. Binding strength may be evaluated by methods such as ELISA and "equilibrium capture" (Clackson T et al. (1991) Nature 352, 624-628, Winter G. et al 1994 loc cit). The eluted phage are then used to infect E. coli and the cycle of rescue and selection is repeated. In order to increase mutations leading to antibodies with better binding properties, bacterial mutator strains may be used or mutations may be introduced in vitro using PCR (Winter G. et al 1994 loc cit). Once high-affinity scFv fragments are isolated, the encoding genes are combined with genes encoding for the desired antibody format, such as monoclonal IgG for the expression in suitable host cells. For the production of libraries of antibodies to be used for expression of bispecific antibodies, it is convenient to use the same VL library to construct binders against the two different target antigens, and to limit its size (Merchant A M et al (1998) Nat. Biotechnol., July 1998, Vol. 16(7), p. 677-681). For single domain antibodies it is sufficient to generate two VH libraries with different antigen specificity.

Example 2

Establishing Libraries of Monoclonal Antibodies by Ribosome Display

Ribosome display offers the opportunity to obtain libraries even more diverse than the ones obtained using phage display and libraries of the size of up to $10^{13}$ individual recombinants have been reported (Hanes and Pluckthun, (1997) Proc. Natl. Acad. Sci. 94, 4937-4942).

For ribosome display, as a first step, B cells are obtained as described in example 1 and mRNA encoding for VH and VL segments is extracted. The mRNA is transcribed to cDNA and the DNA encoding for the VH and the VL chains is amplified by PCR, with primers providing restriction sites and purified. Subsequently the PCR products are ligated with DNA that comprise sequences required for ribosome display including a ribosome binding site, a transcription terminator such as T3Te and the T7 promoter (Krebber et al. (1997), J Immunol Methods. (1997) 201(1): 35-55., Hanes and Pluckthun, (1997) Proc. Natl. Acad. Sci. 94, 4937-4942), Hanes et al. (1998) Proc. Natl. Acad. Sci. 95 (24) 14130-14135). As in example 1 a linker sequence may be added in order to obtain scFv fragments. After amplification by PCR, the ligated PCR products are transcribed in vitro and the resulting mRNA is purified. The mRNA is now translated in vitro using E. coli extract containing ribosomes (Hanes and Pluckthun, (1997 loc cit), Hanes et al. (1998 loc cit)). The translation is stopped using a suitable buffer and the ribosomes carrying the mRNA and the scFv protein are isolated.

The selection of binding proteins is carried out by applying the ribosome mixture to a surface with immobilized antigen and by removing the unbound ribosomes through washing.

The retained ribosome complexes are then dissociated and the mRNA is recovered. The mRNA is then amplified by reverse transcription PCR, purified and used for the next round of ribosome display (Hanes and Pluckthun, (1997 loc cit), Hanes et al. (1998 loc cit)). In order to complete the screening and to obtain scFv protein, PCR products from the last round of ribosome display are cloned into a suitable vector, transcribed and translated in vitro. The scFv fragments are then detected by ELISA. During the various PCR steps mutations leading to diversity of the library are introduced mimicking the natural process of affinity maturation. Other methods to increase diversity are described in by Hanes et al. (1998 loc cit).

As in phage display, once high-affinity scFv fragments are isolated, the encoding genes are combined with genes encoding for the desired antibody format, such as monoclonal IgG for the expression in suitable host cells. For expression of bispecific antibodies two libraries with two different VH chains but the same VL chains are produced. For single domain antibodies, the presence of VL is not required.

Example 3

Chromatographic Analytics for Identification of Monoclonal Antibodies Suitable for Cloning of Bispecific Antibodies Antibodies from two libraries containing monoclonal antibodies with different antigen recognizing sites were subjected to chromatographic analytics using an Agilent HP 1100 series instrument in order to find suitable candidates for the later expression of bispecific antibodies. The stationary phase was Fractogel SO3(S) (Merck, Darmstadt, Germany), that had been packed into a Tricorn column (GE Healthcare, Uppsala, Sweden) of 5 mm diameter and 100 mm length according to the manufacturer's instructions. The analytical method comprised a linear gradient elution using the following buffers: buffer A: 25 mM phosphate; buffer B: 25 mM phosphate, 1.0 M NaCl. The pH of both buffers had been adjusted to pH 6.0 using 8 M NaOH solution. The method was run at a flow rate of 0.5 mL/min at a temperature of 25° C.

Prior to the injection of the antibody, the column was equilibrated by running 0% B for 8 min. The gradient was run from 0% B (0 M NaCl) to 30% B (0.3 M NaCl) in 30 min, followed by a step to 100% B, a hold for 4 min at 100% B, followed by a further step to 0% B and a hold for 8 min. The linear gradient phase serves for eluting the antibody, while potential strongly adsorbed impurities are eluted during the high salt wash after which the column is re-equilibrated.

The injection volume was 40 μL which corresponded to amounts of 20-80 μg of monoclonal antibody, depending on the antibody concentration in the sample. Since these amounts are still far in the analytical range, the experimental method is insensitive to variations of the injection amounts in this magnitude.

The antibody was detected using the diode array detector of the Agilent system at wavelengths of 220 nm and 280 nm and the chromatogram was recorded.

Figure 4:
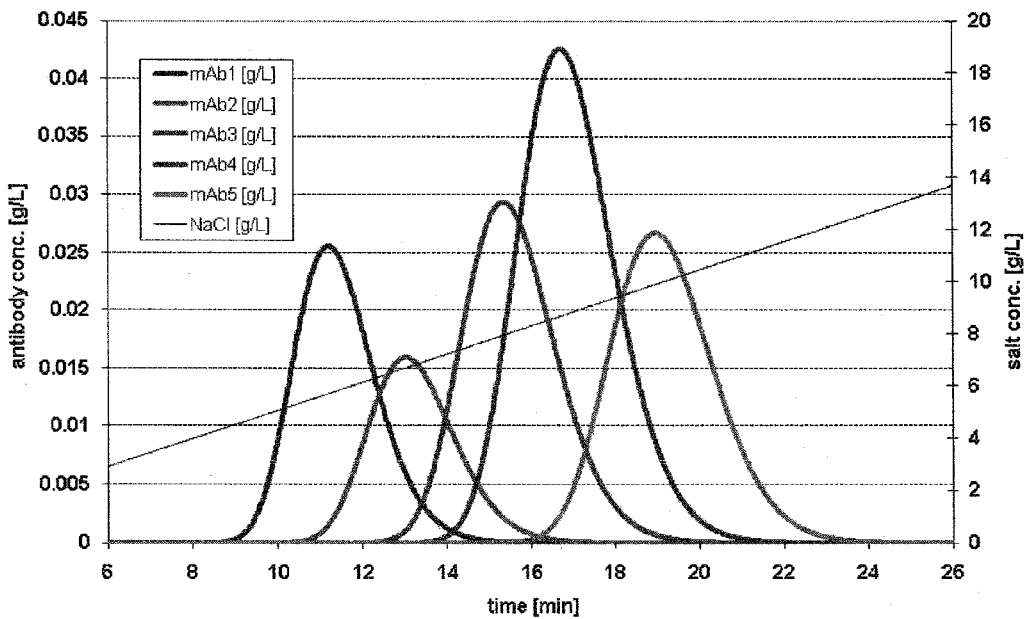
FIG. 4 shows an overlay of five different simulated chromatograms obtained by applying the method described in Example 3 to five monoclonal antibodies from one library, wherein the chromatograms for the antibodies in all libraries are obtained using the same method, and wherein the chromatograms are processed and evaluated according to the method described in Example 4 and Example 5.
Figure 5:
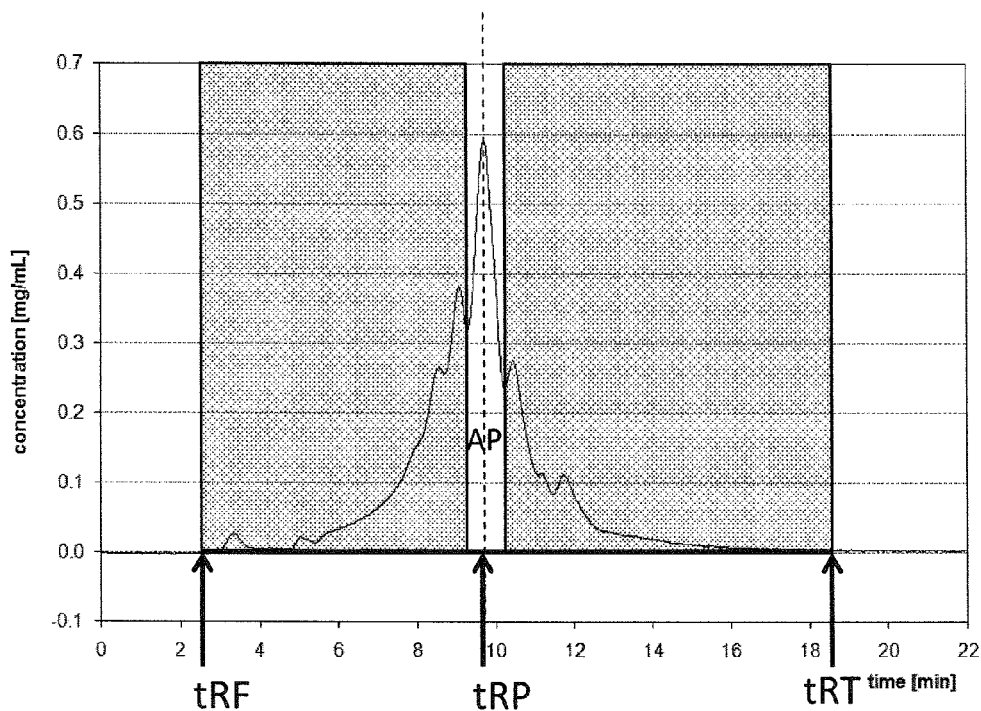
FIG. 5 shows an analytical chromatogram of a monoclonal antibody obtained using a Propac wCX-10 column, wherein the retention times are indicated as follows: peak front tRF, peak maximum of the tallest peak tRP, peak tail tRT. The area of the main peak in the chromatogram, AP, is confined by the valleys in the chromatogram that are closest to the main peak, indicated by the borders of the rectangles that face each other, the baseline and the UV signal, and wherein the total area AT is given by the area between the UV signal and the baseline.
Figure 6:
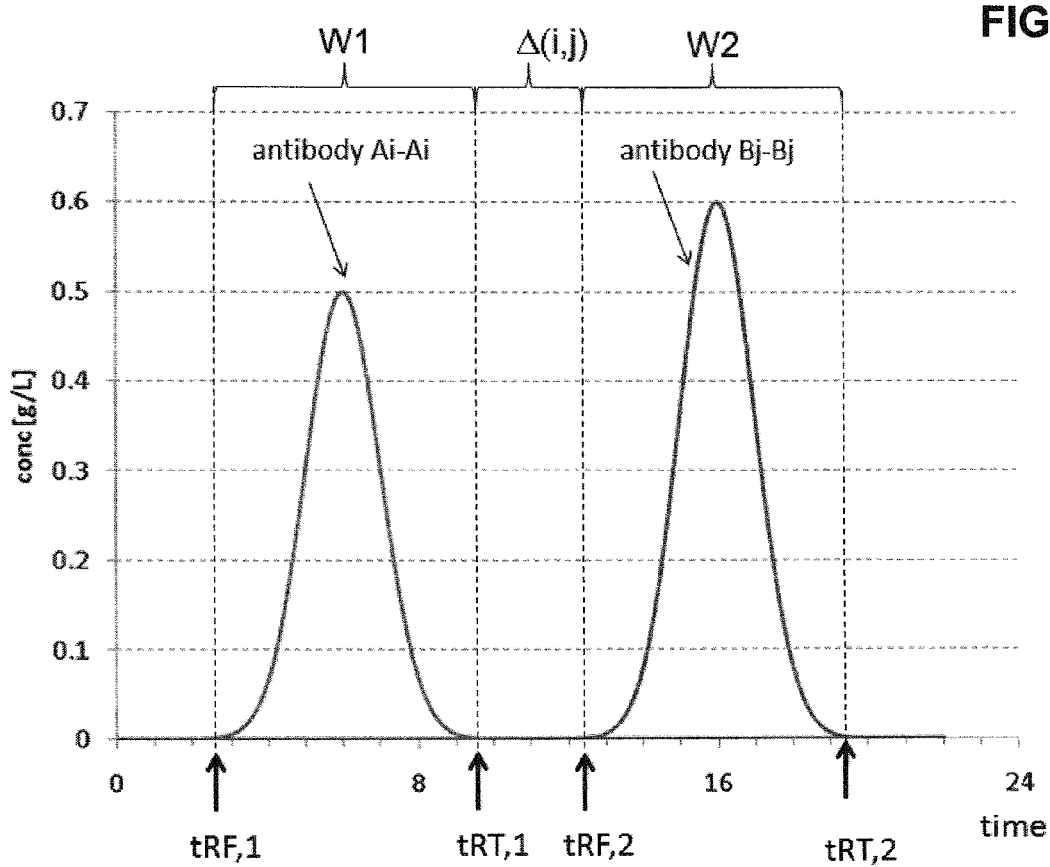
FIG. 6 shows a schematic overview with the evaluation of pairs Ai-Ai and Bj-Bj of monoclonal antibodies, wherein the retention times are indicated as follows: peak front of the first antibody tRF,1; peak tail of the first antibody tRT,1; peak front of the second antibody tRF,2; peak tail of the second antibody tRT,2, and wherein the difference $\Delta(i,j)$ is given by (tRF,2−tRT,1). The peak widths are indicated by W1 and W2, respectively.

The same analytical method was used to analyze all antibodies of the two libraries. An overlay of five simulated typical chromatograms obtained by analyzing five different mAbs using the method described above is show in FIG. 4. Due to the presence of charged isoforms, the antibody may appear very heterogeneous, thus the chromatogram of a monoclonal antibody may display multiple peaks as shown in FIG. 5.

Example 4

Processing of Chromatograms and Data Extraction

Prior to evaluation of the chromatograms recorded using the method described in example 1 a baseline is drawn under the antibody peak. The baseline is drawn such that a maximum of an estimated 0.5% of the total peak area is below baseline. It is important that the baseline be drawn in a consistent manner for the different analyzed chromatograms. For this purpose, also a computer software tool may be used, which is typically included in the software package provided with the HPLC instrument. Consequently, the baseline touches the chromatogram at the peak front and at the peak tail.

The information extraction from the chromatogram is demonstrated in FIG. 5 for an analytical chromatogram of a monoclonal antibody, obtained using a Propac wCX-10 column. The following parameters are obtained:

The retention time of the peak front which corresponds to touching point of the baseline and the chromatogram in the peak front and is termed tRF The retention time of the peak tail which corresponds to touching point of the baseline and the chromatogram in the peak tail and is termed tRT The retention time the peak maximum of the highest peak (main isoform peak), termed tRP The area of the main peak in the chromatogram, confined by the valleys that are closest to the main peak, indicated by inner borders of the rectangles in FIG. 5, the baseline and the chromatogram, termed AP The total peak area, confined by the chromatogram and the baseline, termed AT Example 5

Evaluation of Chromatographic Analytical Data and Antibody Ranking

After having extracted the data from the chromatograms, the purity P of each monoclonal antibody is calculated. In Table 1 the data is summarized for each antibody Ai-Ai from a first example library against a first antigen and Bj-Bj from a second example library second antigen. The antibodies were sorted by their main peak retention time and named A1-A1, A2-A2, A3-A3 etc.

TABLE 1

Evaluation of chromatographic analytical data and antibody ranking according to the Rs and the Δ(i,j) criteria. The highlighted fields indicate the top ranking antibody pairs according to the respective criteria. In the two lower tables the index of A is increasing from top to bottom (i designates a row), and the index of B is increasing from left to right (j designates a column)

| antibody library 1 Ai-Ai | | | | |
|---|---|---|---|---|
| i | tR | tRF | tRT | Purity |
| 1 | 10.0 | 9.0 | 11.5 | 100% |
| 2 | 12.0 | 10.5 | 14.0 | 100% |
| 3 | 13.0 | 11.0 | 13.5 | 93% |
| 4 | 14.0 | 13.0 | 15.5 | 83% |
| 5 | 16.0 | 14.5 | 17.5 | 100% |

| antibody library 2 Bj-Bj | | | | |
|---|---|---|---|---|
| j | tR | tRF | tRT | Purity |
| 1 | 9.0 | 8.0 | 11.0 | 100% |
| 2 | 12.5 | 11.0 | 14.5 | 70% |
| 3 | 14.0 | 13.0 | 14.5 | 100% |
| 4 | 15.0 | 13.5 | 16.0 | 90% |
| 5 | 17.0 | 16.0 | 19.5 | 97% |

| Rs i/j | 1 | 2 | 3 | 4 | 5 |
|---|---|---|---|---|---|
| 1 | 0.27 | 0.83 | 1.75 | 1.80 | 2.50 |
| 2 | 0.85 | 0.14 | 0.60 | 0.83 | 1.57 |
| 3 | 1.00 | 0.17 | 0.75 | 1.00 | 1.83 |
| 4 | 1.73 | 0.50 | 0.25 | 0.20 | 1.17 |
| 5 | 2.17 | 1.00 | 1.00 | 0.45 | 0.54 |

| Δ(i/j) | 1 | 2 | 3 | 4 | 5 |
|---|---|---|---|---|---|
| 1 | -2.0 | -0.5 | 1.5 | 2.0 | 4.5 |
| 2 | -0.5 | -3.0 | -1.0 | -0.5 | 2.0 |
| 3 | 0.0 | -2.5 | -0.5 | 0.0 | 2.5 |
| 4 | 2.0 | -3.0 | -1.5 | -2.0 | 0.5 |
| 5 | 3.5 | 0.0 | 0.0 | -1.5 | -1.5 |

Subsequently, each antibody of the first library Ai-Ai is compared with each antibody of the second library Bj-Bj, as to evaluate each possible combination. The Rs and the Δ(i,j) values were calculated and for each pair (Ai-Ai, Bj-Bj). A purity criterion of 95% was imposed which excludes certain antibodies from the ranking. Both antibodies in the pair (Ai-Ai, Bj-Bj) are required to satisfy the purity criterion.

Finally the antibody pairs are ranked by their Rs values in descending order starting with the largest positive values. The top scoring antibody pairs according to the Rs criterion are (A1-A1, B5-B5), (A5-A5, B1-B1), (A1-A1, B3-B3). Note that some antibody pairs such as (A3-A3, B5-B5) would be ranked higher than (A1-A1, B3-B3) according to the Rs criterion (Rs=1.83 vs. Rs=1.75), but are excluded from the ranking because at least one of the antibodies of the pair does not fulfill the purity criterion.

The top scoring antibody pairs according to the Δ(i,j) criterion are (A1-A1, B5-B5), (A5-A5, B1-B1), (A2-A2, B5-B5). The deviation between the results of the Rs and the Δ(i,j) criterion are due to the different peak widths that are not taken into account by the Δ(i,j) criterion. Nevertheless for the two top scoring antibody pairs the two criteria deliver the same results. The top scoring antibody pairs with the largest Rs or Δ(i,j) values that are fulfilling the purity constraint are selected for cloning of bispecific antibodies.

Example 6

Figure 7:
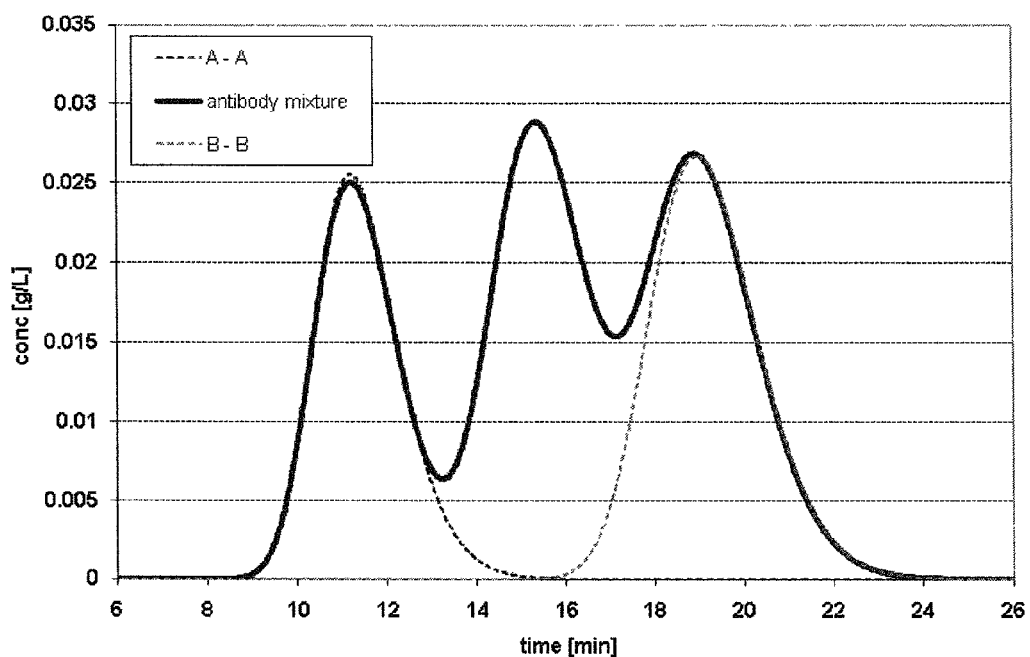
FIG. 7 shows a simulated analytical chromatogram produced with the method described in Example 3 for an injection of 0.02 mg antibody per mL of packed bed volume of the antibody mixture produced by the host cells (thick, solid line), wherein the mixture contains bispecific heterodimeric antibodies (A-B) and homodimeric monoclonal antibodies (A-A, B-B), wherein the simulated chromatograms of injections of pure homodimers A-A and B-B are overlaid and indicated by the dashed lines, and wherein the peak in between the homodimer peaks corresponds to the bispecific antibody A-B.

Expression of Bispecific Antibodies in Host Cells and Chromatographic Analytics of Bispecific Antibodies Bispecific antibodies were expressed in host cells. The antibody mixture produced by the host cells contains the heterodimeric bispecific antibody A-B and the homodimeric monoclonal antibodies A-A and B-B which correspond to the original antibodies from the pair (Ai-Ai, Bj-Bj) that was selected for cloning as described in Example 5. The chromatographic method developed for analyzing all antibodies from the libraries is suited also to analyze the antibody mixture produced by the host cells as the bispecific antibody combines the properties of the A-A antibody and the B-B antibody and will therefore display an elution behavior that is in between that of A-A and B-B. This context is illustrated in FIG. 7 where the simulated chromatograms of the antibody mixture produced by the host cells containing the bispecific antibody and the chromatograms of the A-A and the B-B homodimers from the libraries are superimposed. For the sake of clarity, the heights of the simulated homodimer chromatograms were scaled to match the chromatogram of the mixture.

Example 7

Isolation of Bispecific Antibodies on a Preparative Scale Using Single Column Chromatography After harvest, the cell culture supernatant was passed through two clarification steps comprising a centrifuge and a depth filtration step.

The bispecific antibody contained in the clarified cell culture supernatant was purified using a two-step chromatographic process.

The first chromatographic step was carried out based on protein A affinity chromatography. It served the purpose of removing the largest part of the impurities such as host cell proteins, DNA and media components. However, since protein A cannot distinguish among the different antibody species, it does not contribute to the purification of the bispecific antibody from the antibody mixture.

The second chromatographic step was carried out using the same stationary phase, i.e. Fractogel SO3(S), the same buffers and the same method that is described in Example 3 except for the column cleaning which was extended and included a cleaning-in-place step using 1 M NaOH and the protein load was increased by a factor of 1000 from 0.02 to 20 mg protein per mL of packed bed volume. The protein A eluate was loaded directly without buffer exchange. The linear flow rate was 150 cm/h throughout the run.

Figure 8:
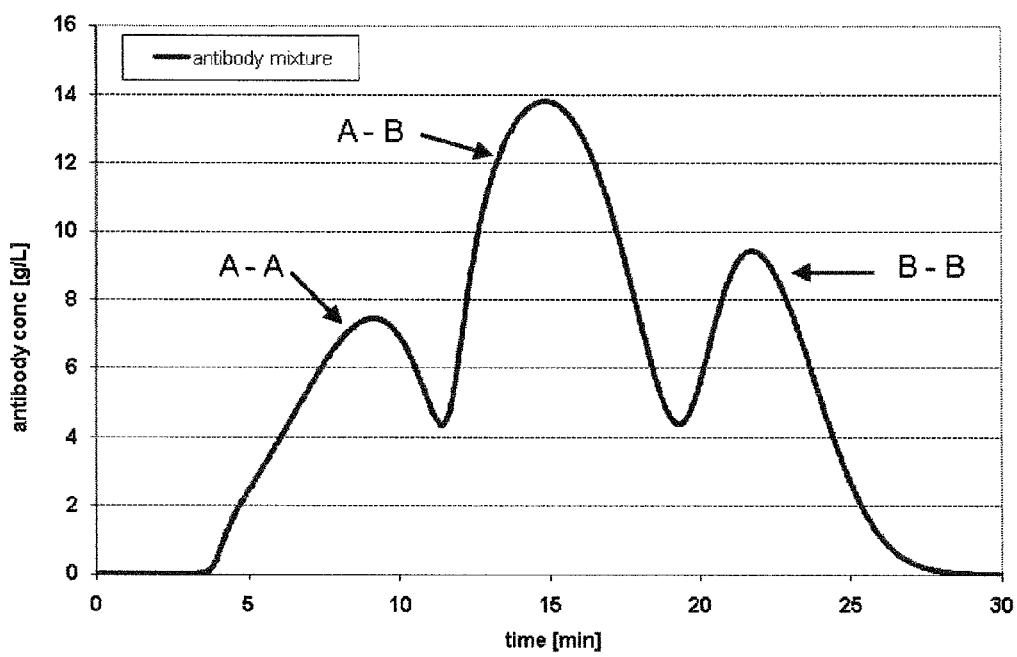
FIG. 8 shows a preparative single column chromatogram obtained applying the method described in Example 7 for an injection of 20 mg antibody per mL of packed bed volume of the antibody mixture of bispecific heterodimers (A-B) and homodimers (A-A, B-B) produced by the host cells.

A simulated chromatogram of the purification is provided in FIG. 8. The results of the simulations further show that the yield of the bispecific antibody with an ideal peak fractionation is 78% for a purity of 99.8% at a productivity of 12 mg pure product per mL of packed bed volume per hour. In practice the yield for the desired purity will be much lower since the product peak fractionation needs to be carried out leaving safety margins towards the product peak front and tail.

In FIG. 8 the portions of the chromatogram indicated by the grey rectangles contain parts of the bispecific antibody peak that are overlapping with the peaks of the homodimers and that have to be therefore discarded, which explains the low yield.

Example 8

Isolation of Bispecific Antibodies on a Preparative Scale Using Continuous Countercurrent Chromatography (MCSGP)

The clarification of the cell culture supernatant and the first chromatography step using protein A affinity chromatography was carried out as described in Example 7: Isolation of bispecific antibodies on a preparative scale using single column chromatography.

Subsequently, multicolumn countercurrent solvent gradient purification (MCSGP) was applied as a second purification step instead of single column chromatography.

MCSGP was carried out using the same stationary phase, i.e. Fractogel SO3(S) and the same buffers as described in Examples 3 and 7, respectively. The MCSGP process was operated in a three-column configuration as described in FIG. 3 in Biotechnology and Bioengineering 100(6): 1166-1177 with the operating parameters listed in Table 2.

TABLE 2

MCSGP operating parameters. Nomenclature as reported in Biotechnology and Bioengineering 100(6): 1166-1177, FIG. 3

| | | |
|---|---|---|
| Q1 | [cm/h] | 150 |
| Q2 | [cm/h] | 45 |
| Q3 | [cm/h] | 75 |
| Q4 | [cm/h] | 105 |
| Qfeed | [cm/h] | 138 |
| Q6 | [cm/h] | 0 |
| c1 | [g/L] | 60.0-60.0 |
| c2 | [g/L] | 8.0-8.0 |
| c3 | [g/L] | 8.0-8.0 |
| c4 | [g/L] | 0.0-8.0 |
| cFeed | [g/L] | Feed |
| c6 | [g/L] | 1.0-1.0 |
| tCC | [min] | 14.0 |
| tBL | [min] | 8.0 |

Figure 9:
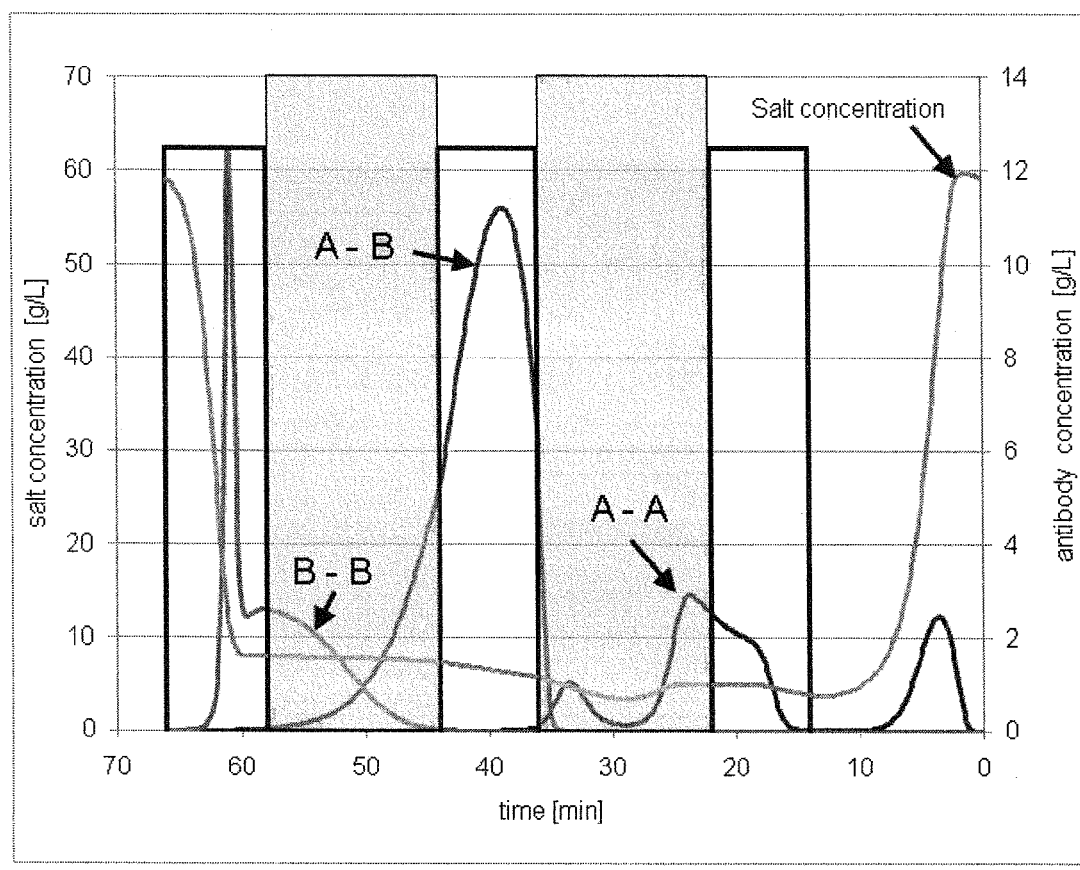
FIG. 9 shows a simulated internal MCSGP profile obtained applying the method described in Example 8 for preparative purification of the antibody mixture of bispecific heterodimers (A-B) and homodimers (A-A, B-B) produced by the host cells, wherein it is to be noted that the time axis is inverted; the profile is to be seen in analogy to a batch chromatogram and is cyclically repeated; the parts of the chromatogram indicated with the shaded rectangles correspond to sections of the chromatogram that are internally recycled; the part of the chromatogram in between the shaded rectangle corresponds to the product elution window.

A simulated internal chromatogram of the purification using MCSGP is provided in FIG. 9. The results of the simulations show that the yield of the bispecific antibody is 99.9% for a purity of 99.8% at a productivity of 25 mg pure product per mL of packed bed volume per hour. Thus by using MCSGP, the yield could be increased by more than 20% and maximized and the productivity could be more than doubled.

The invention claimed is:

1. A method for the identification of a purifyable multi-specific polypeptide species (AiBj) which is a multimer consisting of at least two different specificity polypeptide chains (Ai, Bj), the method comprising the following steps:
   (A) generation of a library of nucleic acids for each of the different specificity polypeptide chains (A, B) forming the multimer, and narrowing the library size through antigen binding and/or activity assays;
   (B) individually expressing a sufficient amount of polypeptide chains (A1, A2, A3, . . . An; B1, B2, B3, . . . Bm) with each individual library member, and forming homomultimers therefrom;
   (C) using chromatography, for the determination of an analytically discriminative parameter, for each of the homomultimers;

(D) selecting at least one pair (AiAi, BjBj) of homomultimers of different specificity polypeptide chains which are analytically sufficiently discriminated;

(E) expressing the polypeptide chains from the library of step (A) corresponding to the homomultimers identified in step (D) in host cells such that a ternary mixture of homomultimers (AiAi; BjBj) and heteromultimers (AiBj) is produced by culture of the host cells; and (F) purifying the resulting ternary mixture by using chromatography.

2. The method according to claim 1, wherein the steps (A)-(D) are repeated until a pair can be identified, which is analytically sufficiently discriminated in at least one of the following relative parameters: resolution (Rs), relative retention time (RRT), retention time, retention time difference, retention volume purity.

3. The method according to claim 1, wherein for the discrimination in step (D) a relative retention time (RRT) in a chromatographic separation of smaller than 0.9 and larger than 1.1 is used.

4. The method according to claim 1, wherein as a criterion for the selection in step (D) at least one of the following relative parameters is used: resolution (Rs), relative retention time (RRT), retention time, retention time difference, retention volume, purity.

5. The method according to claim 1, wherein the antibodies are dimers formed from polypeptides A and B, the heterodimer being a bispecific antibody, each polypeptide A and B comprising a heavy polypeptide chain with at least one heavy chain variable region.

6. The method according to claim 1, wherein the antibodies are dimers formed from polypeptides A and B, the heterodimer being a bispecific antibody, each polypeptide A and B comprising: a heavy polypeptide chain with at least one heavy chain variable region; and a light polypeptide chain with a light chain variable region or a corresponding scaffold peptide.

7. The method according to claim 1, wherein the heavy polypeptide chain comprises at least one heavy chain constant region or a corresponding scaffold peptide.

8. The method of claim 7, wherein the heavy chain constant regions are of the IgG, IgA, IgM, IgD or IgE class.

9. The method according to claim 3, wherein in step (F) for the purification of a ternary mixture of dimeric antibodies of the type AA, AB, BB, for the separation of the three components for the isolation of the multi-specific fraction AB multicolumn countercurrent solvent gradient purification chromatography with a stationary phase load of more than 1 mg antibody mixture per milliliter packed bed volume is used.

10. The method according to claim 3, wherein in step (F) for the purification of a ternary mixture of dimeric antibodies of the type AA, AB, BB, for the separation of the three components multicolumn countercurrent solvent gradient purification chromatography with a stationary phase load of more than 1 mg antibody mixture per milliliter packed bed volume is used.

11. The method according to claim 10, wherein the antibodies are dimers formed from polypeptides A and B, the heterodimer being a bispecific antibody, each polypeptide A and B comprising a heavy polypeptide chain with at least one heavy chain variable region.

12. The method d according to claim 10, wherein the antibodies are dimers formed from polypeptides A and B, the heterodimer being a bispecific antibody, each polypeptide A and B comprising: a heavy polypeptide chain with at least one heavy chain variable region; and a light polypeptide chain with a light chain variable region or a corresponding scaffold peptide.

13. The method according to claim 10, wherein the heavy polypeptide chain comprises at least one heavy chain constant region or a corresponding scaffold peptide.

14. The method of claim 13, wherein the heavy chain constant regions are of the IgG, IgA, IgM, IgD or IgE class.

15. The method according to claim 10, wherein a chromatographic stationary phase with a mean particle diameter of less than 70 micrometers is used.

16. The method of claim 13, wherein the heavy chain constant regions are of the IgG, IgA, IgM, IgD or IgE class, wherein the heavy chain constant regions are selected from the group of IgG1 and IgG4, or IgG1 and IgG2 subclasses.

17. The method according to claim 10, wherein a chromatographic stationary phase with a mean particle diameter of in the range of 2-35 micrometers, wherein the width of the distribution (2σ) is in the range of +/−50% of the mean value.

18. A method for the identification of a purifyable multi-specific polypeptide species (AiBj) which is a multimer consisting of at least two different specificity polypeptide chains (Ai, Bj), a heterodimeric bispecific antibody, the method comprising the following steps:

(A) generation of a library of nucleic acids for each of the different specificity polypeptide chains (A, B) forming the multimer, using array technologies, phage display, yeast display or ribosome display and narrowing the library size through antigen binding and/or activity assays;

(B) individually expressing a sufficient amount of polypeptide chains (A1, A2, A3, . . . An; B1, B2, B3, . . . Bm) with each individual library member, and forming homomultimers therefrom, homodimers (A1A1, A2A2, A3A3, . . . AnAn; B1B1, B2B2, B3B3, BmBm);

(C) using chromatography in single-column mode or isoelectric focusing, for the determination of an analytically discriminative parameter, the chromatographic retention time, for each of the homomultimers;

(D) selecting at least one pair (AiAi, BjBj) of homomultimers of different specificity polypeptide chains which are analytically sufficiently discriminated;

(E) expressing the polypeptide chains from the library of step (A) corresponding to the homomultimers identified in step (D) in host cells such that a ternary mixture of homomultimers (AiAi; BjBj) and heteromultimers (AiBj) is produced by culture of the host cells;

(F) purifying the resulting ternary mixture by using chromatography.

19. The method of claim 7, wherein the heavy chain constant regions are of the IgG, IgA, IgM, IgD or IgE class, wherein the heavy chain constant regions are selected from the group of IgG1 and IgG4, or IgG1 and IgG2 subclasses.

* * * * *